US012690996B2

(12) United States Patent
Daggett

(10) Patent No.: US 12,690,996 B2
(45) Date of Patent: Jul. 28, 2026

(54) NASAL CONFORMER DEVICES, SYSTEMS, AND METHODS

(71) Applicant: Justin Daggett, Louisville, TN (US)

(72) Inventor: Justin Daggett, Louisville, TN (US)

(*) Notice: Subject to any disclaimer, the term of this patent is extended or adjusted under 35 U.S.C. 154(b) by 44 days.

(21) Appl. No.: 18/959,879

(22) Filed: Nov. 26, 2024

(65) Prior Publication Data

US 2025/0205074 A1 Jun. 26, 2025

Related U.S. Application Data

(60) Provisional application No. 63/613,264, filed on Dec. 21, 2023.

(51) Int. Cl.
A61F 5/08 (2006.01)
(52) U.S. Cl.
CPC ..................................... A61F 5/08 (2013.01)
(58) Field of Classification Search
CPC ...... A61F 5/05; A61F 5/56; A61F 2/18; A61F 2/186; A61M 15/08; A61M 16/0666; A62B 23/06
See application file for complete search history.

(56) References Cited

U.S. PATENT DOCUMENTS

2008/0009897 A1* 1/2008 Duran Von Arx ........ A61F 5/08
606/199

2014/0261459 A1* 9/2014 Santelli, Jr. ............ A61K 33/38
53/473
2023/0355420 A1* 11/2023 Shetye ....................... A61F 5/08

FOREIGN PATENT DOCUMENTS

RU 2477088 C1 * 3/2013 ............... A61F 5/08

OTHER PUBLICATIONS

English Machine Translation of Description of RU 2477088 C1 (Ivanov) from Patentscope website<https://patentscope.wipo.int/search/en/detail.jsf?docId=RU92316965> accessed Mar. 6, 2026 (Year: 2026).*
English Machine Translation of Abstract of RU 2477088 C1 (Ivanov) from Patentscope website<https://patentscope.wipo.int/search/en/detail.jsf?docId=RU92316965> accessed Mar. 6, 2026 (Year: 2026).*

* cited by examiner

*Primary Examiner* — Diane D Yabut
(74) *Attorney, Agent, or Firm* — Robinson IP Law, PLLC

(57) ABSTRACT

Various implementations include an anatomical nasal conformer device. The device includes a first stent and a second stent each being configured to be inserted into a different nostril of a user. Each of the first stent and the second stent define an opening extending along a centerline from an anterior end of the stent to a posterior end of the stent. The centerline includes a posterior portion adjacent the posterior end, an anterior portion adjacent the anterior end, and a middle portion disposed between the posterior portion and the anterior portion. The anterior portion of the centerline and the posterior portion of the centerline form an angle. The angle is in the range of 90 to 65 degrees.

19 Claims, 8 Drawing Sheets

NASAL CONFORMER DEVICES, SYSTEMS, AND METHODS

BACKGROUND

After certain corrective and cosmetic surgeries, the tissue of the nose can become misshapen. Past nasal conformers include relatively straight tubular stents that are placed inside the nose of the user to help support and shape the nostril. However, the nasal cavity is not a straight channel and includes multiple bends and recesses. Thus, these past nasal conformers fail to properly fit the nasal cavity of the user. The recesses of the nasal cavities remain unfilled by the stents of the conformers, which leads to poor contact of the device such that the device can be easily dislodged (e.g., by a sneeze). This also leads to excess pressure being placed on the tissue that is in contact with the stents, causing irritation and tissue damage.

Furthermore, past nasal conformers do not account for different sizes and shapes of noses (e.g., of different ages and ethnicities) and do not provide a means for larger changes.

SUMMARY

Various implementations include an anatomical nasal conformer device. The device includes a first stent and a second stent each being configured to be inserted into a different nostril of a user. Each of the first stent and the second stent define an opening extending along a centerline from an anterior end of the stent to a posterior end of the stent. The centerline includes a posterior portion adjacent the posterior end, an anterior portion adjacent the anterior end, and a middle portion disposed between the posterior portion and the anterior portion. The anterior portion of the centerline and the posterior portion of the centerline form an angle. The angle is in the range of 90 to 65 degrees.

In some implementations, the angle is in the range of 80 to 75 degrees.

In some implementations, the angle is a first angle. In some implementations, the middle portion of the centerline and the posterior portion of the centerline form a second angle. In some implementations, the second angle is in the range of 35 to 55 degrees. In some implementations, the second angle is in the range of 40 to 50 degrees.

In some implementations, the first stent and the second stent each include a nostril dome supporting protrusion extending anteriorly from an outer surface of the stent adjacent the intersection of the anterior portion of the centerline and the middle portion of the centerline. In some implementations, the nostril dome supporting protrusion of each of the first stent and the second stent further extend medially.

In some implementations, the nostril dome supporting protrusion is configured to be disposed posteriorly to a nasal aperture margin when the first stent and the second stent are inserted into the nostrils of a user. In some implementations, the nostril dome supporting protrusion is configured to apply pressure to a deep margin of the lower lateral cartilage when the first stent and the second stent are inserted into the nostrils of a user.

In some implementations, the first stent and the second stent each include a lateral ala vestibule protrusion extending laterally from an outer surface of the stent adjacent the anterior portion of the centerline. In some implementations, the first stent and the second stent each include an infradome recessed portion disposed between the nostril dome supporting protrusion and the lateral ala vestibule protrusion.

In some implementations, the lateral ala vestibule protrusion is configured to be disposed posteriorly to a nasal aperture margin when the first stent and the second stent are inserted into the nostrils of a user. In some implementations, the lateral ala vestibule protrusion is configured to apply pressure to a lateral aspect of a nasal vestibule when the first stent and the second stent are inserted into the nostrils of a user.

In some implementations, the device further includes a central bridge extending between and coupling together the anterior end of the first stent and the anterior end of the second stent. In some implementations, the device further includes a handle protrusion extending from the central bridge.

Various other implementations include an anatomical nasal conformer system. The system includes a first anatomical nasal conformer device and a second anatomical nasal conformer device. Each device includes a first stent and a second stent each being configured to be inserted into a different nostril of a user. Each of the first stent and the second stent define an opening extending along a centerline from an anterior end of the stent to a posterior end of the stent. The centerline includes a posterior portion adjacent the posterior end, an anterior portion adjacent the anterior end, and a middle portion disposed between the posterior portion and the anterior portion. The anterior portion of the centerline and the posterior portion of the centerline form an oblique angle. The first stent and the second stent each include a nostril dome supporting protrusion extending anteriorly from an outer surface of the stent adjacent the intersection of the anterior portion of the centerline and the middle portion of the centerline. The nostril dome supporting protrusion extends from the outer surface by a length. The anterior portion includes a nasal aperture portion configured to abut the nasal aperture margin when the first stent and the second stent are inserted into the nostrils of the user. The nasal aperture portion has a longest width as measured perpendicular to the centerline. One of the length of the nostril dome supporting protrusion or the longest width of the nasal aperture portion is larger for the second anatomical nasal conformer device than the one of the first anatomical nasal conformer device.

In some implementations, the oblique angle is in the range of 90 to 65 degrees. In some implementations, the oblique angle is in the range of 80 to 75 degrees.

In some implementations, the oblique angle is a first angle. In some implementations, the middle portion of the centerline and the posterior portion of the centerline form a second angle. In some implementations, the second angle is in the range of 35 to 55 degrees. In some implementations, the second angle is in the range of 40 to 50 degrees.

In some implementations, the first stent and the second stent each include a nostril dome supporting protrusion extending anteriorly from an outer surface of the stent adjacent the intersection of the anterior portion of the centerline and the middle portion of the centerline. In some implementations, the nostril dome supporting protrusion of each of the first stent and the second stent further extend medially.

In some implementations, the nostril dome supporting protrusion is configured to extend beyond the nasal aperture margin when the first stent and the second stent are inserted into the nostrils of a user. In some implementations, the nostril dome supporting protrusion is configured to apply pressure to the deep margin of the lower lateral cartilage when the first stent and the second stent are inserted into the nostrils of a user.

In some implementations, the first stent and the second stent each include a lateral ala vestibule protrusion extending laterally from an outer surface of the stent adjacent the anterior portion of the centerline. In some implementations, the first stent and the second stent each include an infradome recessed portion disposed between the nostril dome supporting protrusion and the lateral ala vestibule protrusion.

In some implementations, the lateral ala vestibule protrusion is configured to be disposed posteriorly to the nasal aperture margin when the first stent and the second stent are inserted into the nostrils of a user. In some implementations, the lateral ala vestibule protrusion is configured to apply pressure to a lateral aspect of the nasal vestibule when the first stent and the second stent are inserted into the nostrils of a user.

In some implementations, the device further includes a central bridge extending between and coupling together the anterior end of the first stent and the anterior end of the second stent. In some implementations, the device further includes a handle protrusion extending from the central bridge.

BRIEF DESCRIPTION OF DRAWINGS

Example features and implementations of the present disclosure are disclosed in the accompanying drawings. However, the present disclosure is not limited to the precise arrangements and instrumentalities shown. Similar elements in different implementations are designated using the same reference numerals.

DETAILED DESCRIPTION

Figure 1:
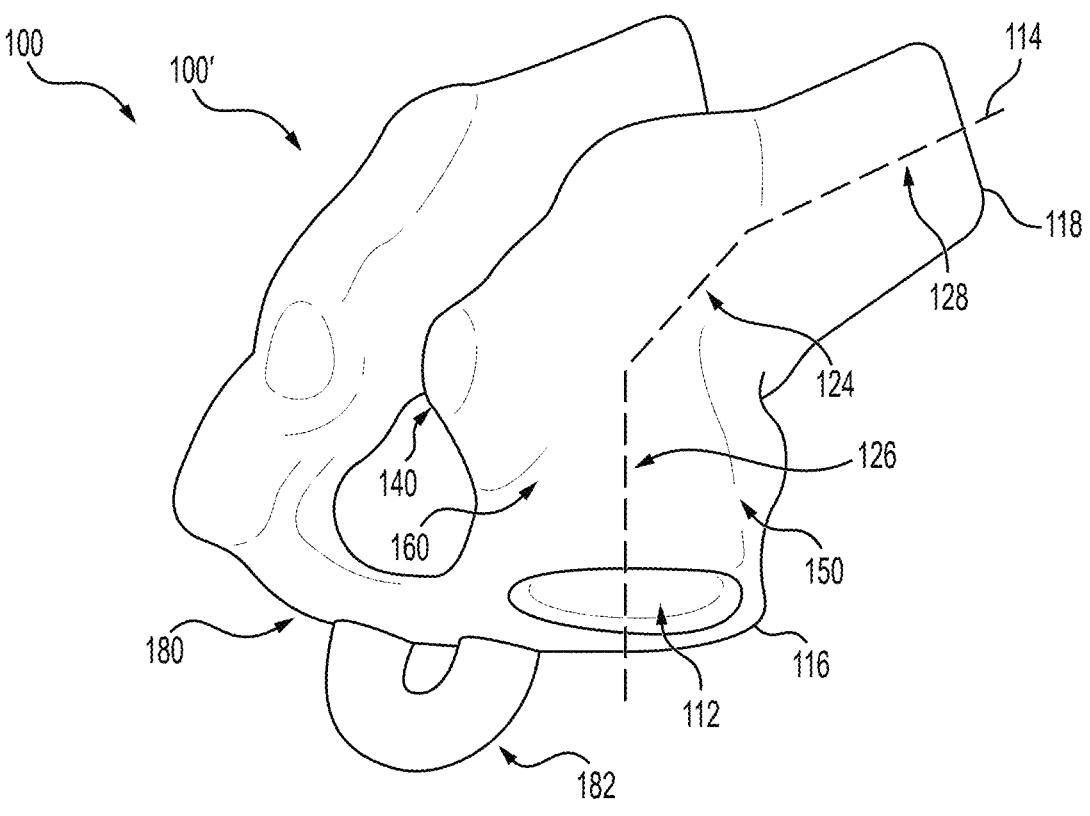
FIG. 1 is a perspective view of an anatomical nasal conformer device, according to one implementation.
Figure 2:
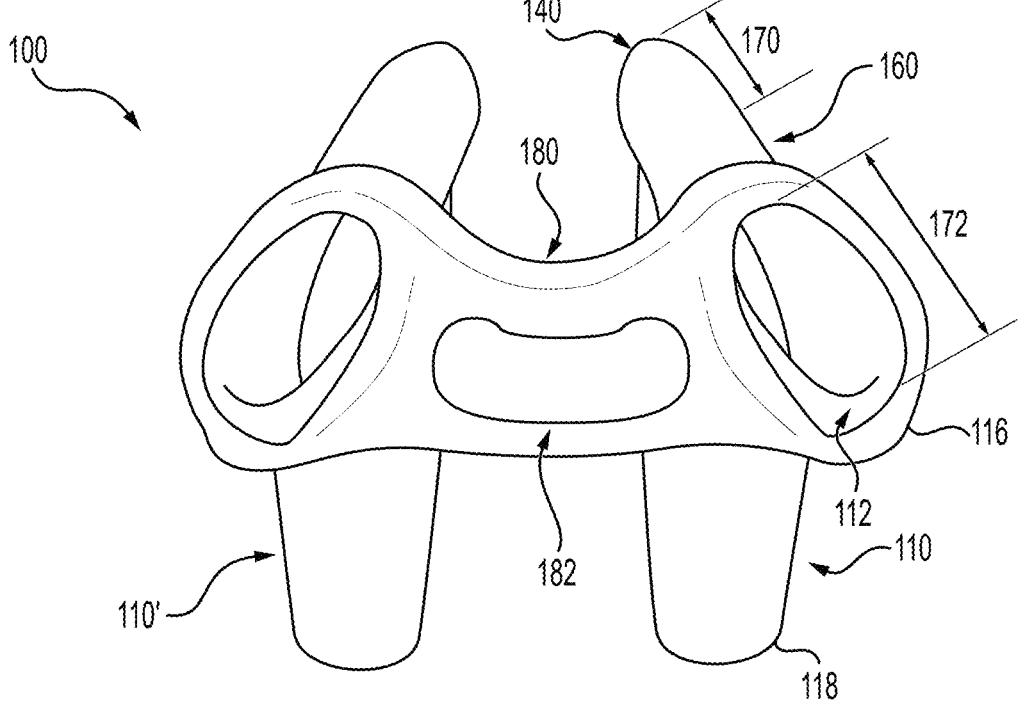
FIG. 2 is a bottom perspective view of the nasal apertures of the anatomical nasal conformer device of FIG. 1.
Figure 3:
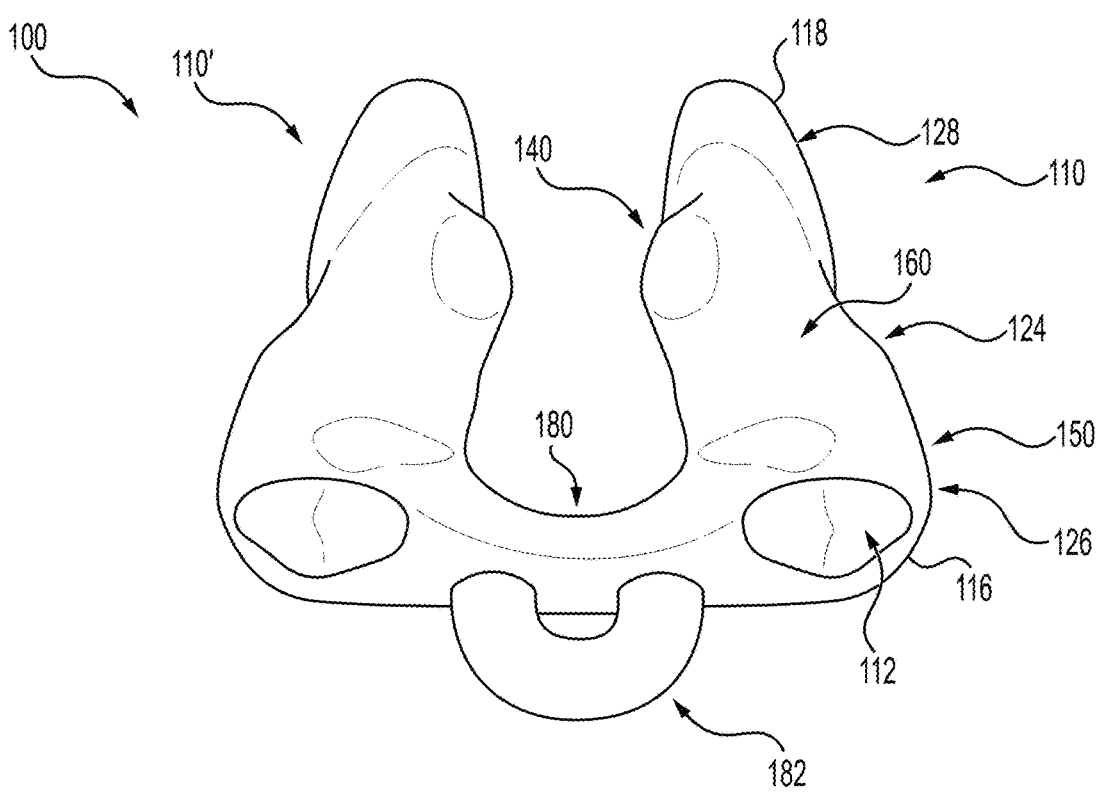
FIG. 3 is an anterior view of the nasal apertures of the anatomical nasal conformer device of FIG. 1.
Figure 4:
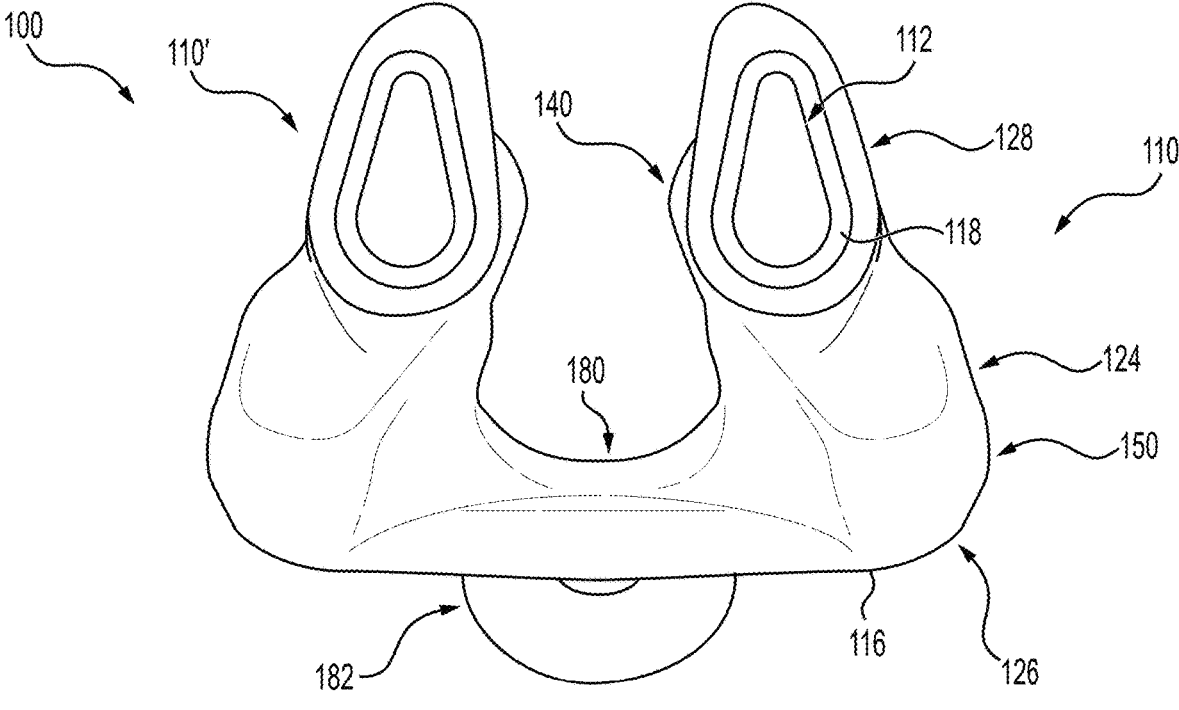
FIG. 4 is a posterior view of the nasal apertures of the anatomical nasal conformer device of FIG. 1.
Figure 5:
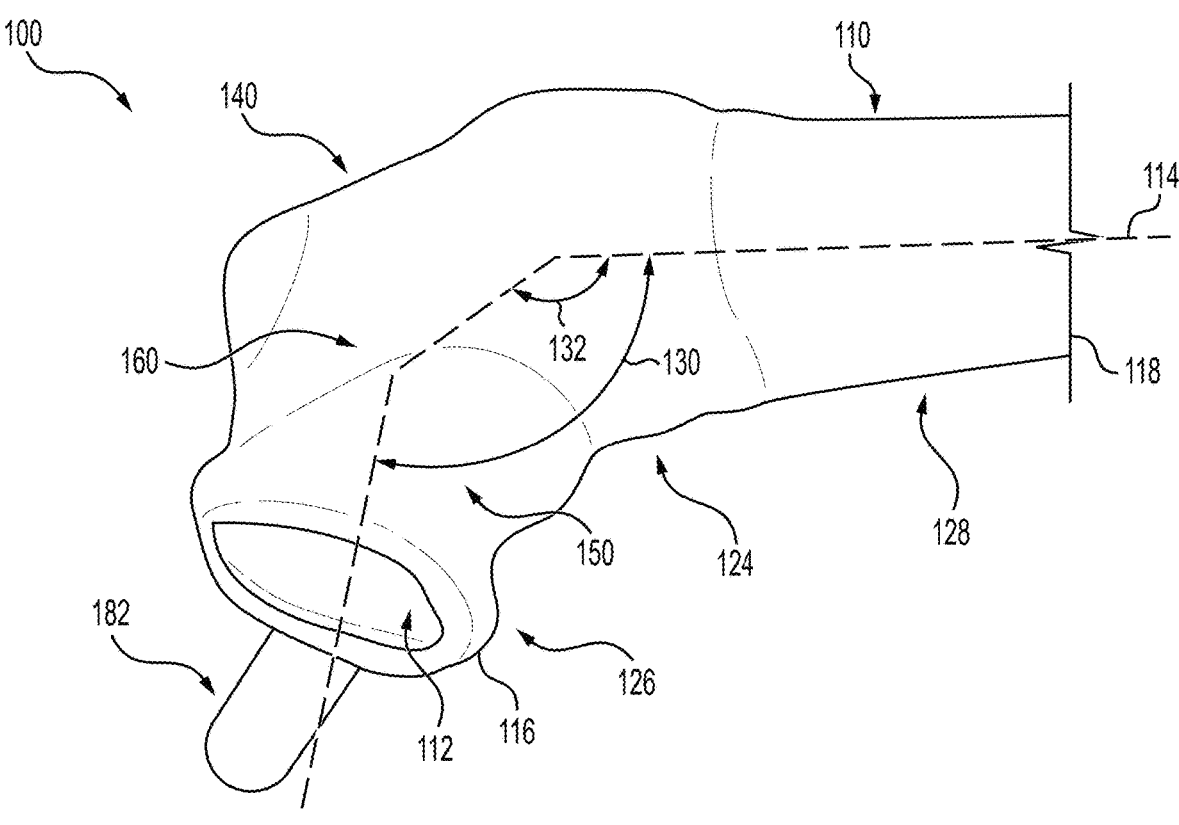
FIG. 5 is a left side view of the nasal apertures of the anatomical nasal conformer device of FIG. 1.
Figure 6:
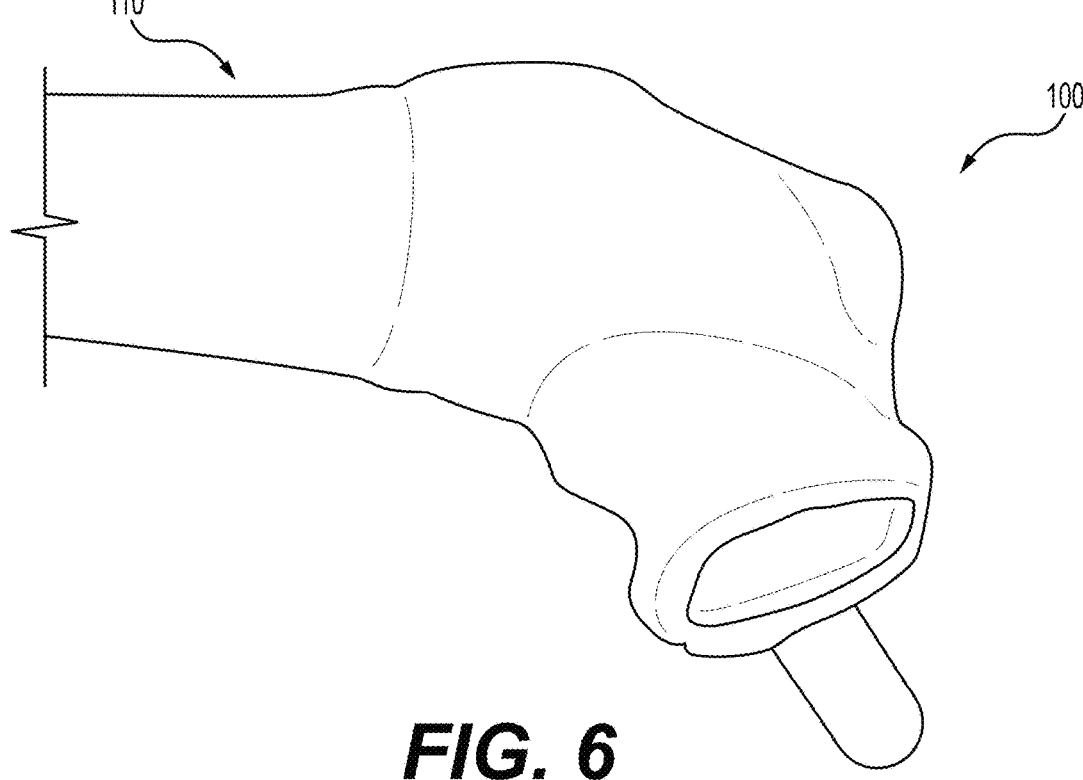
FIG. 6 is a right side view of the nasal apertures of the anatomical nasal conformer device of FIG. 1.
Figures 7, 8:
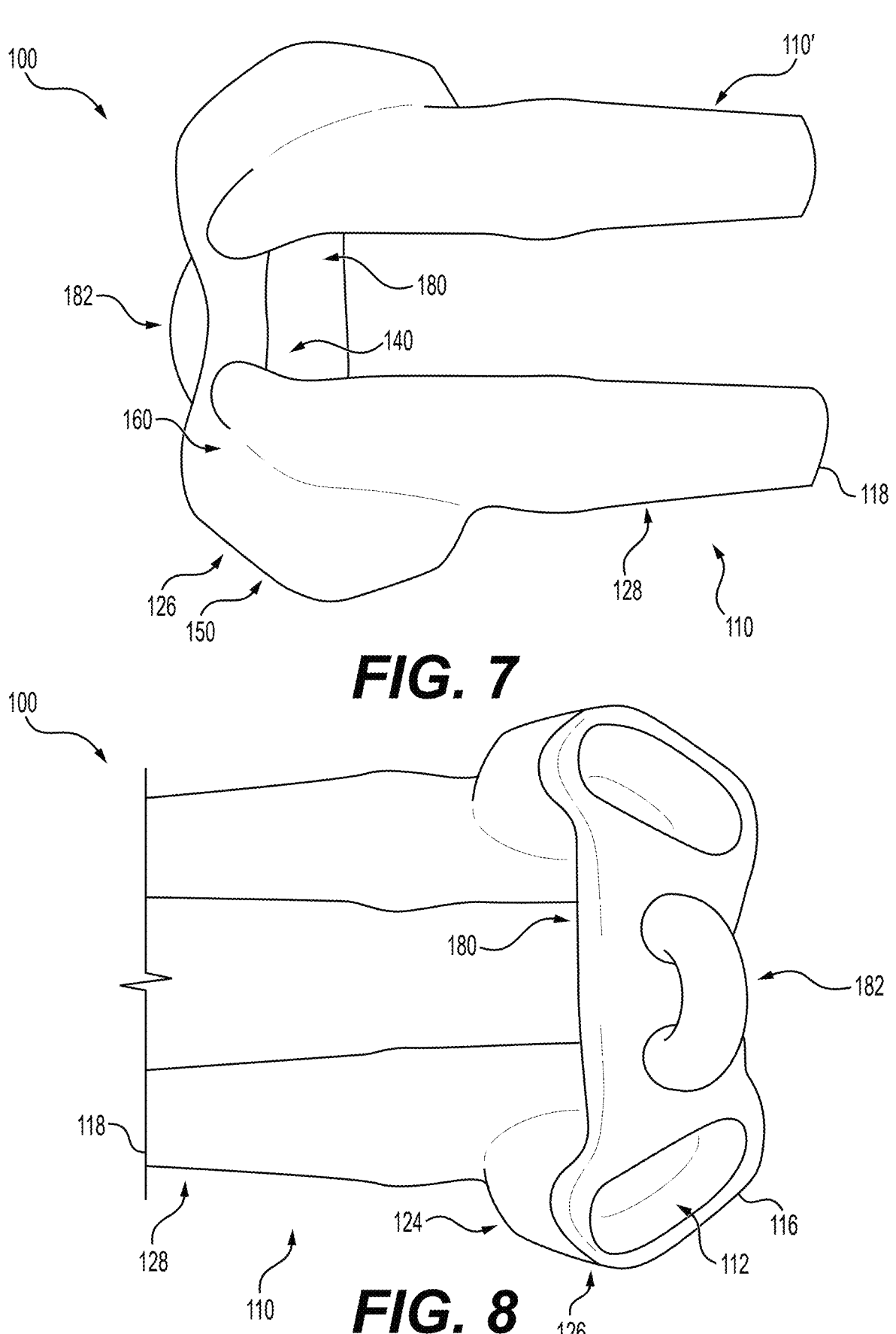
FIG. 7 is a top view of the nasal apertures of the anatomical nasal conformer device of FIG. 1.
FIG. 8 is a bottom view of the nasal apertures of the anatomical nasal conformer device of FIG. 1.

The devices, systems, and methods disclosed herein provide for anatomical nasal conformer devices for causing the nose of a user to conform to a desired shape. Each device includes two stents and a central bridge coupling them together. The stents are each disposed within the nostril of a user to place pressure on selected tissue within the nasal cavity to cause the tissue to conform to a desired shape.

The stents of each device include an anterior portion, a posterior portion, and a middle portion between the anterior portion and the posterior portion. The centerline of each portion is at an oblique angle to the other portions to better fit the bends of the nasal cavity.

The stents also include a nostril dome supporting protrusion to fill and place pressure on the nasal aperture margin and a lateral ala vestibule protrusion to fill and place pressure on the lateral aspect of the nasal vestibule. The result of these protrusions is to cause these recesses in the nasal cavity to be supported and to conform to a desired shape.

The anatomical nasal conformer devices disclosed herein can be a component of an anatomical nasal conformer system. The anatomical nasal conformer devices of the system have progressively larger features such that once the nose of the user has conformed to one anatomical nasal conformer device, a subsequent and larger dimensioned anatomical nasal conformer device can be used to further conform the user's nose.

The anatomical nasal conformer devices can also be sized for different ages and for different ethnicities, as discussed herein.

Various implementations include an anatomical nasal conformer device. The device includes a first stent and a second stent each being configured to be inserted into a different nostril of a user. Each of the first stent and the second stent define an opening extending along a centerline from an anterior end of the stent to a posterior end of the stent. The centerline includes a posterior portion adjacent the posterior end, an anterior portion adjacent the anterior end, and a middle portion disposed between the posterior portion and the anterior portion. The anterior portion of the centerline and the posterior portion of the centerline form an angle. The angle is in the range of 90 to 65 degrees.

FIGS. 1-8 show an anatomical nasal conformer device 100, according to one implementation. The device 100 includes a first stent 110, a second stent 110', a central bridge 180, and a handle protrusion 182.

The first stent 110 and the second stent 110' each define an opening 112 extending along a centerline 114 from an anterior end 116 of the stent 110, 110' to a posterior end 118 of the stent 110, 110'. The central bridge 180 extends from the anterior end 116 of the first stent 110 to the anterior end 116 of the second stent 110'. Each of the first stent 110 and the second stent 110' are configured to be inserted into a different nostril of a user. The first stent 110 and second stent 110' are substantially mirrored images of each other across a medial plane that runs perpendicular to a longitudinal axis of the central bridge 180.

Figure 9:
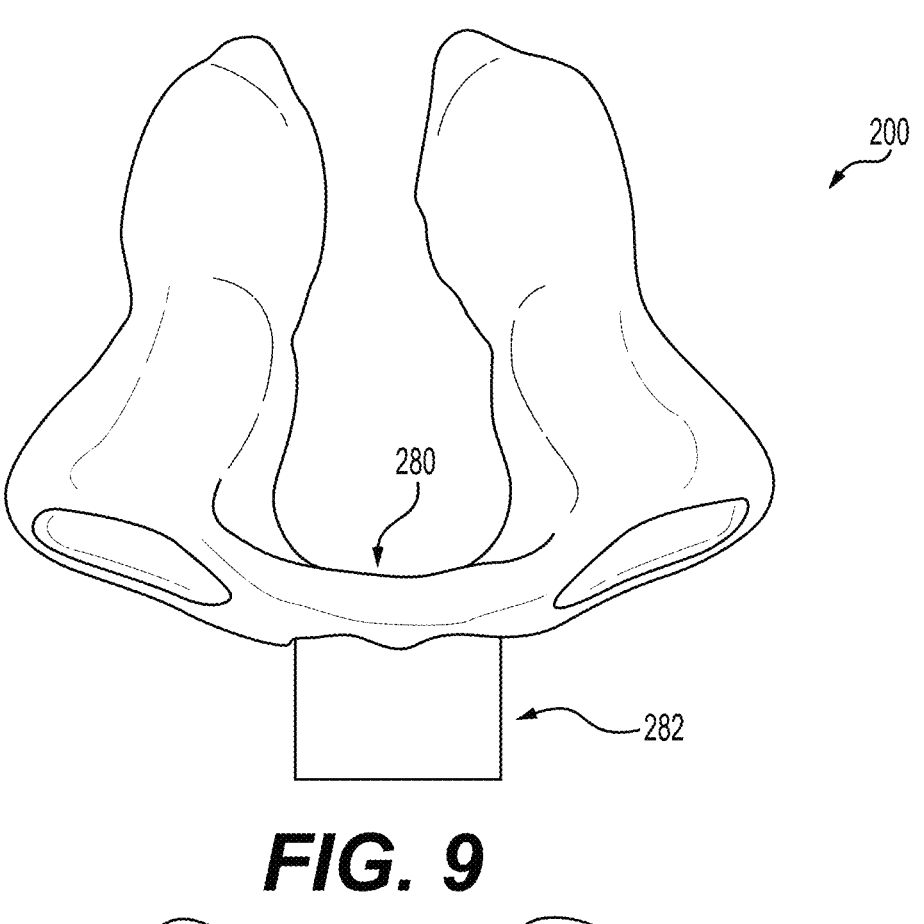
FIG. 9 is an anterior view of an anatomical nasal conformer device, according to another implementation.
Figure 10:
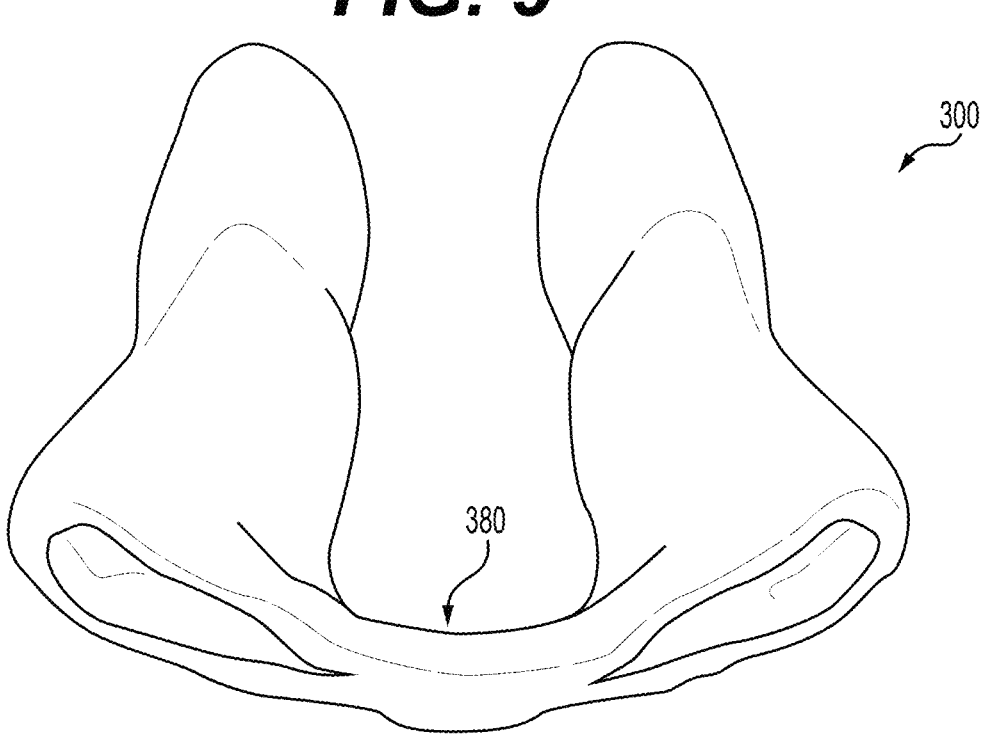
FIG. 10 is an anterior view of an anatomical nasal conformer device, according to another implementation.
Figures 11A, 11B:
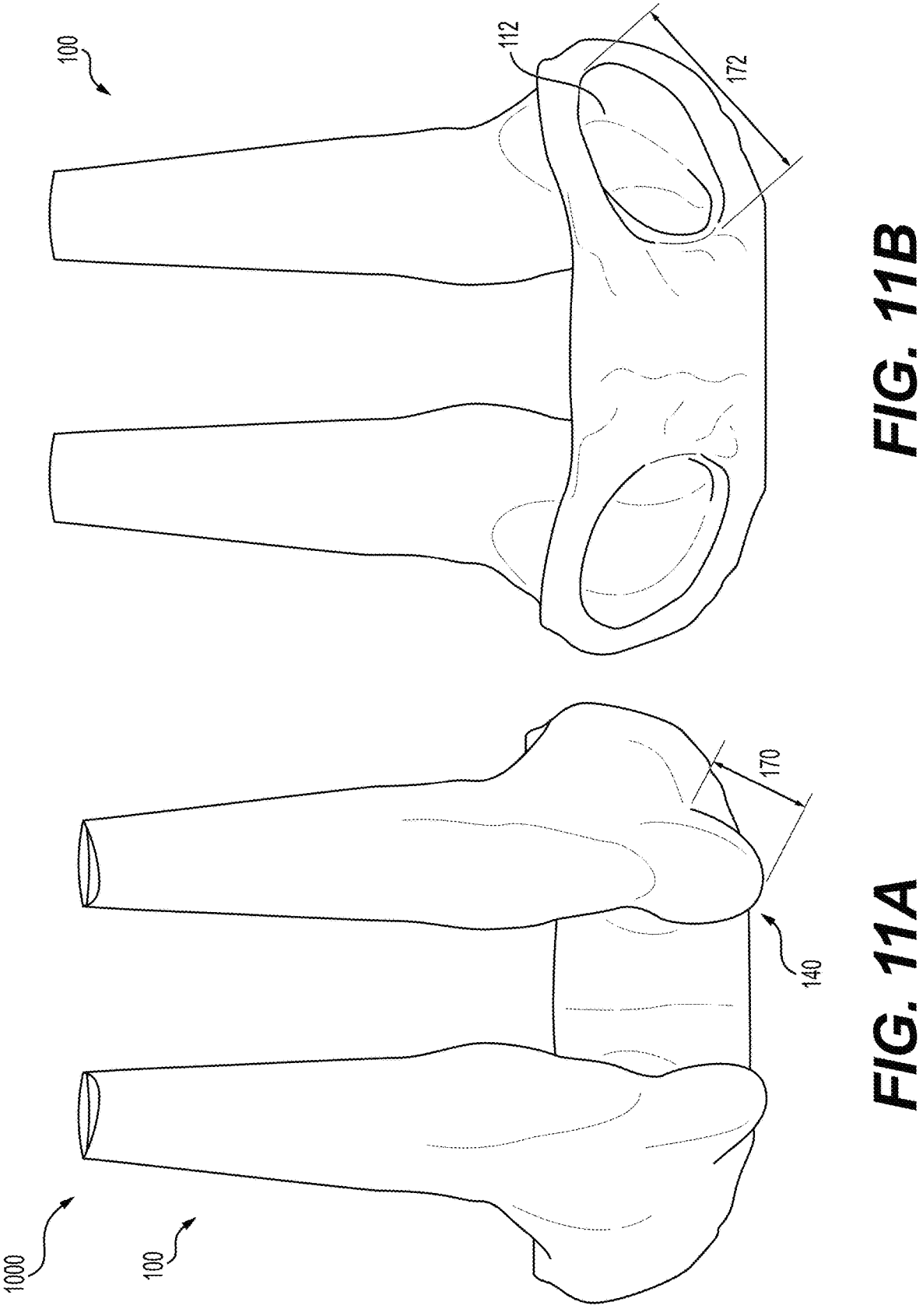
FIG. 11A is a top view of a first anatomical nasal conformer device of an anatomical nasal conformer system, according to one implementation.
FIG. 11B is a bottom view of the first anatomical nasal conformer device of FIG. 11A.
Figures 12A, 12B:
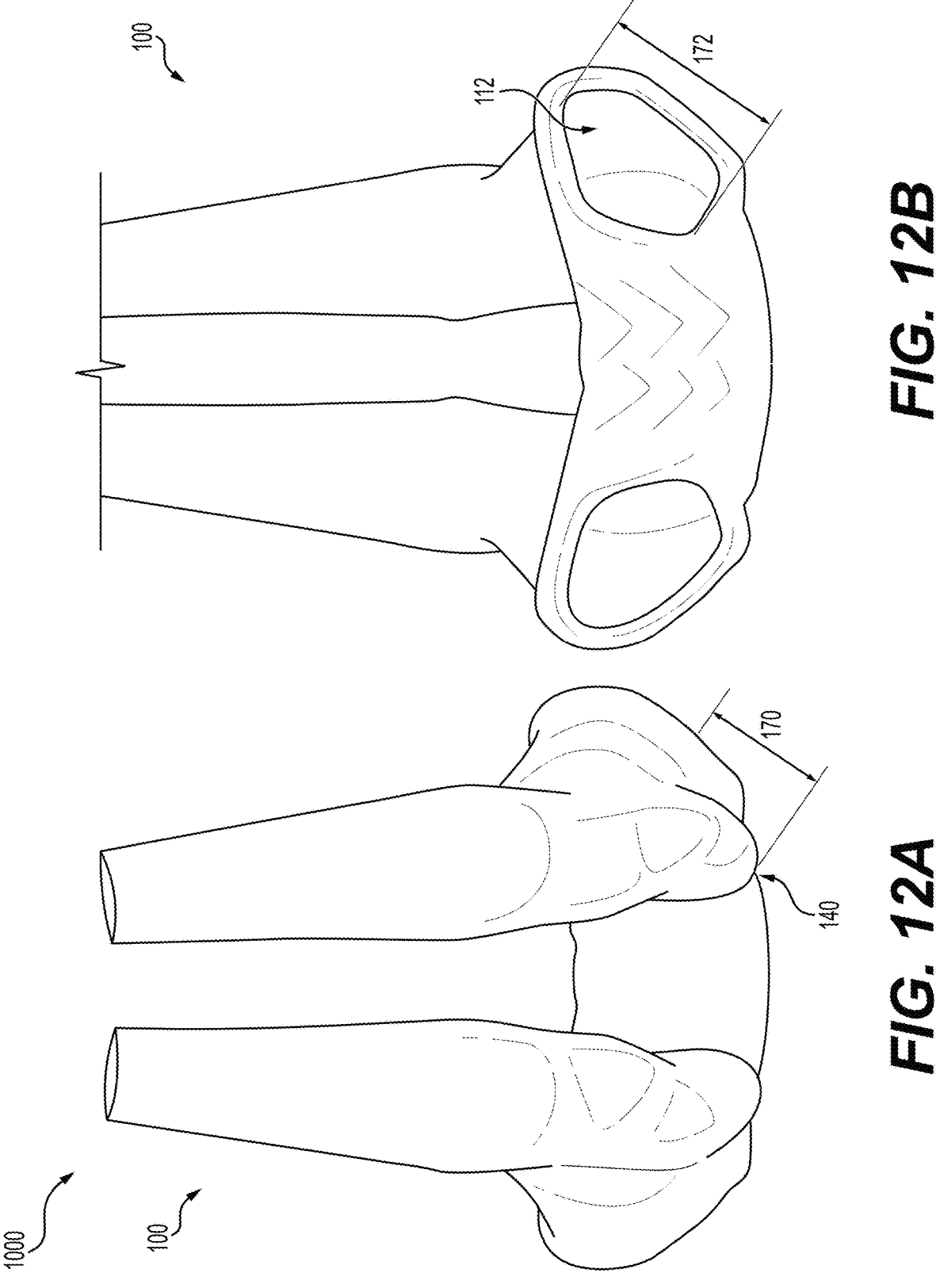
FIG. 12A is a top view of a second anatomical nasal conformer device of the anatomical nasal conformer system of FIG. 11A.
FIG. 12B is a bottom view of the second anatomical nasal conformer device of FIG. 12A.
Figures 13A, 13B:
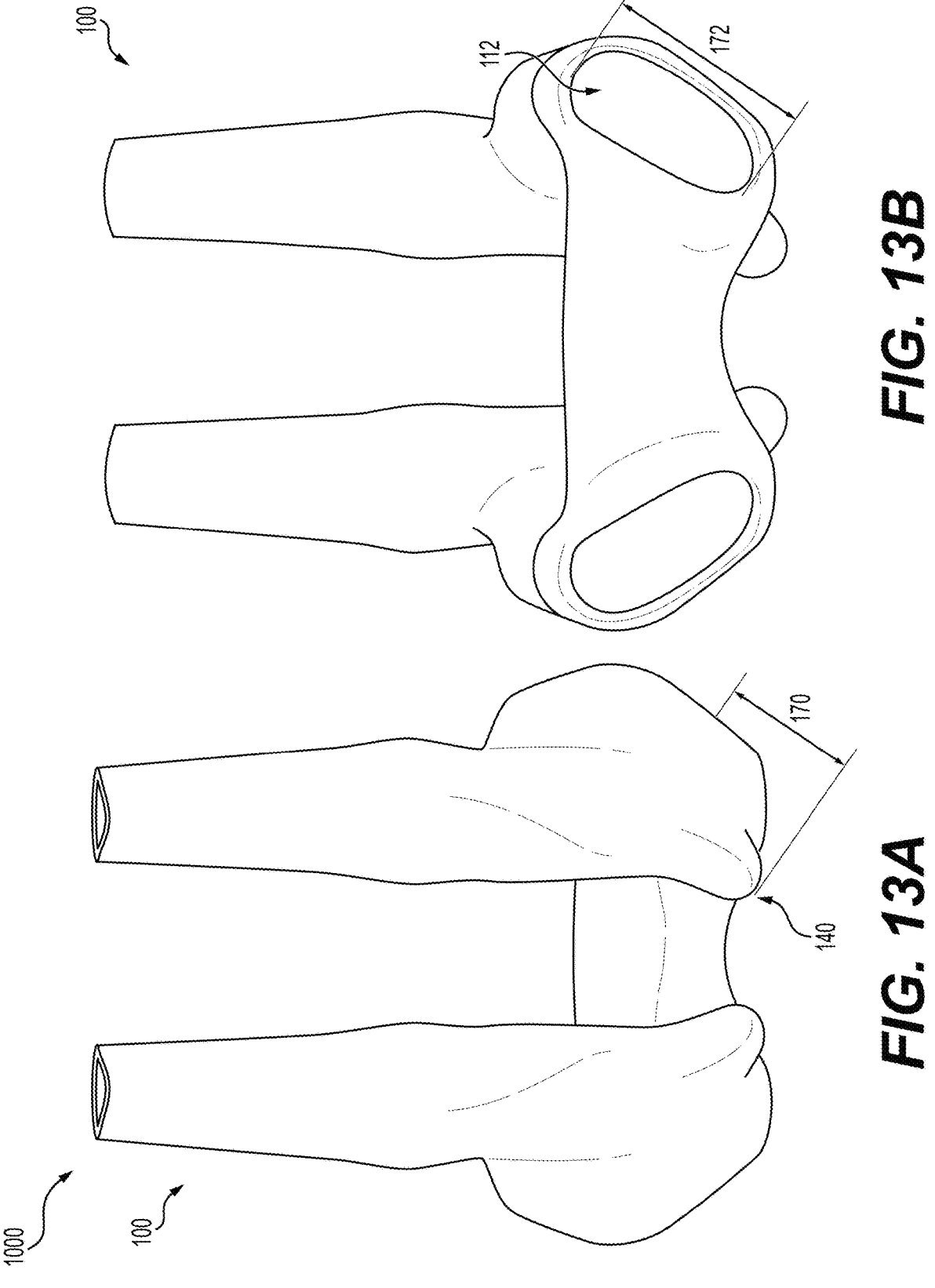
FIG. 13A is a top view of a third anatomical nasal conformer device of the anatomical nasal conformer system of FIG. 11A.
FIG. 13B is a bottom view of the third anatomical nasal conformer device of FIG. 13A.

The handle protrusion 182 extends away from the central bridge 180 in an anterior and/or inferior direction when the first stent 110 and the second stent 110' are disposed within the nostrils of a user. The handle protrusion 182 shown in FIGS. 1-8 is a small prominent ring emanating from the central bridge 180 of the device 100. However, in some implementations, such as the device 200 shown in FIG. 9, the handle protrusion 282 can be a small tab emanating from the central bridge 280 of the device 200. In some implementations, such as the device 300 shown in FIG. 10, the device 300 does not include a handle protrusion extending from the central bridge 380. The handle protrusion 182 can run externally across the columella of the nose to help remove the device 100 by allowing it to be grasped and pulled gently downward.

The centerline 114 includes an anterior portion 126 adjacent the anterior end 116, a posterior portion 128 adjacent the posterior end 118, and a middle portion 124 disposed between the posterior portion 128 and the anterior portion 126. When disposed within the nostrils of a user, the centerline 114 of the posterior portion 128 is substantially perpendicular to the horizontal nasal floor. This allows the nasal conformer device 100 to rest in the normal air space inferior to the inferior turbinate maximizing airflow while minimizing discomfort.

The anterior portion 126 of the centerline 114 and the posterior portion 128 of the centerline 114 shown in FIGS. 1-8 form a first angle 130 of about 80 degrees. However, in some implementations, the first angle is in the range of 80 to 75 degrees. In some implementations, the first angle is in the range of 90 to 65 degrees. The first angle 130 causes the centerline 114 to follow the axis of the normal nasal aperture.

The middle portion 124 of the centerline 114 and the posterior portion 128 of the centerline 114 further form a second angle 132. The second angle 132 shown in FIGS. 1-8 is 45 degrees. However, in some implementations, the second angle is in the range of 40 to 50 degrees. In some implementations, the second angle is in the range of 35 to 55 degrees. The second angle 132 corresponds to the anatomical region including the dome of the nasal aperture, the transition across the piriform aperture (i.e., the bony opening of the nose), and the internal nasal valve (i.e., the junction between the outer, cartilaginous nasal airspace and the inner, bony airspace).

Compared to existing nasal stents that have a straight body, the first angle 130 and the second angle 132 of the stents 100, 110' of the conformer devices 100 disclosed herein better match the natural multi-angled axis of the nasal passage. This makes the stents 110, 110' of the conformer devices 100 more comfortable for the user during use, minimizes impact and pressure from the stents 110, 110' on surrounding sensitive nasal tissues, and maximizes nasal air flow through the stents 110, 110'.

The first stent 110 and the second stent 110' each include a nostril dome supporting protrusion 140 extending from an outer surface of the stent 110, 110' adjacent the intersection of the anterior portion 126 of the centerline 114 and the middle portion 124 of the centerline 114. The nostril dome supporting protrusion 140 extends in a direction having anterior and medial components. The nostril dome supporting protrusion 140 is configured to be disposed posteriorly to a nasal aperture margin when the first stent 110 and the second stent 110' are inserted into the nostrils of a user such that it applies pressure to the deep margin of the lower lateral cartilage of the nostrils of the user.

The nostril dome is the anterior most extent of the nasal airspace projecting beyond the tip of the nostril opening. This corresponds to the genu or bend of the lower lateral cartilages of the nose where they turn direction. This bend of the paired cartilages is what defines the tip of the nose. Internally, the mucosa of the nostril dome is closely adherent to the underside of the cartilage. The nostril dome supporting protrusions 140 of the stents 110, 110' disclosed herein project beyond the nasal aperture margin in order to allow for pressure to be applied directly to the deep margin of the lower lateral cartilage and nasal tip. This avoids excess pressure on the alar margins or soft triangle of the user's nose. It also serves to key the nasal conformer device 100 in place and prevent its dislodgement with sneezing, crying, or rubbing.

The first stent 110 and the second stent 110' of the device 100 shown in FIGS. 1-8 each include a lateral ala vestibule protrusion 150 extending laterally from an outer surface of the stent 110, 110' adjacent the anterior portion 126 of the centerline 114. The lateral ala vestibule protrusion 150 is configured to be disposed posteriorly to a nasal aperture margin when the first stent 110 and the second stent 110' are inserted into the nostrils of a user such that it applies pressure to a lateral aspect of a nasal vestibule of the nostrils of the user.

The lateral aspect of the nasal vestibule is located just inside the external nasal aperture. The lateral ala vestibule protrusion corresponds to this natural hollowing and also allows for good contact and prevention of scar contracture for lateral intranasal incisions.

Between the nostril dome supporting protrusion 140 and the lateral ala vestibule protrusion 150 of the first stent 110 and the second stent 110', each stent 110, 110' includes an infradome recessed portion 160. Inferior to the nostril dome supporting protrusion 140 corresponding to the nostril dome, each stent 110, 110' includes a slight recess or decreased prominence in order to avoid pressure on the ala margin and soft triangle of the nose. These areas of the nostril are very sensitive to breakdown and ulceration which can be significantly deforming to the nasal appearance. The infradome recessed portion 160 allows for increased pressure to be applied in projecting the nasal tip without risking injury to these key areas.

Various other implementations include an anatomical nasal conformer system. The system includes at least a first anatomical nasal conformer device 100 and a second anatomical nasal conformer device 100. However, in some implementations, the system can include three or more anatomical nasal conformer devices 100, as discussed herein.

As described above, each device 100 includes a first stent 110 and a second stent 110' each being configured to be inserted into a different nostril of a user. Each of the first stent 110 and the second stent 110' define an opening 112 extending along a centerline 114 from an anterior end 116 of the stent 110, 110' to a posterior end 118 of the stent 110, 110'. The centerline 114 includes a posterior portion 128 adjacent the posterior end 118, an anterior portion 126 adjacent the anterior end 116, and a middle portion 124 disposed between the posterior portion 128 and the anterior portion 126. The anterior portion 126 of the centerline 114 and the posterior portion 128 of the centerline 114 form an oblique angle. The first stent 110 and the second stent 110' each include a nostril dome supporting protrusion 140 extending anteriorly from an outer surface of the stent 110, 110' adjacent the intersection of the anterior portion 126 of the centerline 114 and the middle portion 124 of the centerline 114. The nostril dome supporting protrusion 140 extends from the outer surface by a length 170. The anterior portion 126 includes a nasal aperture portion configured to abut the nasal aperture margin when the first stent 110 and the second stent 110' are inserted into the nostrils of the user. The nasal aperture portion has a longest width 172 as measured perpendicular to the centerline 114.

FIGS. 11A-13B show three anatomical nasal conformer devices 100 of an anatomical nasal conformer system 1000. Within the system 1000, the length 170 of the nostril dome supporting protrusion 140 and the longest width 172 of the nasal aperture portion is larger for the second anatomical nasal conformer device 100 than the one of the first anatomical nasal conformer device 100. Also, the shape of the nostril dome supporting protrusion 140 and the shape of the nasal aperture portion is different for the second anatomical nasal conformer device 100 than the first anatomical nasal conformer device 100.

Furthermore, the length 170 of the nostril dome supporting protrusion 140 and the longest width 172 of the nasal aperture portion is larger for the third anatomical nasal conformer device 100 than the one of the second anatomical nasal conformer device 100. Also, the shape of the nostril dome supporting protrusion 140 and the shape of the nasal aperture portion is different for the third anatomical nasal conformer device 100 than the second anatomical nasal conformer device 100.

The system 1000 of anatomical nasal conformer devices 100 allows for both ethnically specific stenting as well as progressive long-term molding of the nasal cartilage system. This is done through a series of stent devices 100 with progressively increasing projection in the prominence in the nostril dome and/or in a progressive elongation of the anterior cross-sectional axis of the nasal opening (the cross-sectional axis of the nostril from the tip of the nose toward the corner of the lip). This allows for reshaping both of the nasal cartilage as well as the nasal opening.

Use of the devices 100 in a system 1000, such as the one shown in FIGS. 11A-13B, has demonstrated a less projected overall shape with a wider nasal opening compared to its length. This corresponds to the typical appearance of the cleft nose after cleft repair as well as to ethnic noses consistent with many African and Asian ethnicities. With each stage, the prominence is increased until the final stage demonstrates significantly more projection of the nostril dome as well as elongation of the nostril opening more typical for the western, Caucasian nose.

In use, each of the first stent 110 and the second stent 110' of the first anatomical nasal conformer device 100 is disposed in a different nostril of the user. The stents 110, 110' of the device 100 are configured such that the posterior portion 128 of the stent 110, 110' extends substantially parallel with the nasal floor and the central bridge 180 is adjacent the nasal apertures. In this position, the nostril dome supporting protrusion 140 abuts the deep margin of the lower lateral cartilage and the lateral ala vestibule protrusion 150 abuts the lateral aspect of a nasal vestibule. The shapes of the nostril dome supporting protrusion 140 and the lateral ala vestibule protrusion 150 help to key the stents in place to prevent the device 100 from being inadvertently dislodged.

After a period of time, the nose of the user has ideally conformed to the shape of the first anatomical nasal conformer device 100. The first anatomical nasal conformer device 100 is removed (e.g., by grasping and applying downward force to the handle protrusion) and the first stent 110 and the second stent 110' of a second anatomical nasal conformer device 100 are disposed within the nostrils of the user. The second anatomical nasal conformer device 100 includes a larger length 170 of the nostril dome supporting protrusion 140 and/or a larger longest width 172 of the nasal aperture portion than the first anatomical nasal conformer device 100, which applies further pressure to the regions of the nose that had previously conformed to the shape of the first anatomical nasal conformer device 100. The same steps can be repeated for the second anatomical nasal conformer device 100, and subsequent anatomical nasal conformer devices 100, as were used for the first anatomical nasal conformer device 100. The progression of dimensions of the anatomical nasal conformer devices 100 cause the nose of the user to gradually conform to a final desired shape and size of the final anatomical nasal conformer device 100 in the series of devices 100 in the system 1000.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device are disclosed herein, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An anatomical nasal conformer device, the device comprising:
   a first stent and a second stent each being configured to be inserted into a different nostril of a user, each of the first stent and the second stent defining an opening extending along a centerline from an anterior end of the stent to a posterior end of the stent, wherein the centerline includes a posterior portion adjacent the posterior end, an anterior portion adjacent the anterior end, and a middle portion disposed between the posterior portion and the anterior portion, wherein the anterior portion of the centerline and the posterior portion of the centerline form an angle, wherein the angle is in the range of 90 to 65 degrees, wherein the first stent and the second stent each include a nostril dome supporting protrusion extending from an outer surface of the stent adjacent the intersection of the anterior portion of the centerline and the middle portion of the centerline, wherein the nostril dome supporting protrusion extends in a direction having anterior and medial components.

2. The device of claim 1, wherein the angle is in the range of 80 to 75 degrees.

3. The device of claim 1, wherein the angle is a first angle, wherein the middle portion of the centerline and the posterior portion of the centerline form a second angle, wherein the second angle is in the range of 35 to 55 degrees.

4. The device of claim 1, wherein the nostril dome supporting protrusion of each of the first stent and the second stent further extend medially.

5. The device of claim 1, wherein the nostril dome supporting protrusion is configured to be disposed posteriorly to a nasal aperture margin and to apply pressure to a deep margin of the lower lateral cartilage when the first stent and the second stent are inserted into the nostrils of a user.

6. The device of claim 1, wherein the first stent and the second stent each include a lateral ala vestibule protrusion extending laterally from an outer surface of the stent adjacent the anterior portion of the centerline, wherein the first stent and the second stent each include an infradome recessed portion disposed between the nostril dome supporting protrusion and the lateral ala vestibule protrusion.

7. The device of claim 1, wherein the first stent and the second stent each include a lateral ala vestibule protrusion extending laterally from an outer surface of the stent adjacent the anterior portion of the centerline.

8. The device of claim 7, wherein the lateral ala vestibule protrusion is configured to be disposed posteriorly to a nasal aperture margin and to apply pressure to a lateral aspect of the nasal vestibule when the first stent and the second stent are inserted into the nostrils of a user.

9. The device of claim 1, further comprising a central bridge extending between and coupling together the anterior end of the first stent and the anterior end of the second stent, wherein a handle protrusion extends from the central bridge.

10. An anatomical nasal conformer system, the system comprising:
   a first anatomical nasal conformer device and a second anatomical nasal conformer device each comprising:
      a first stent and a second stent each being configured to be inserted into a different nostril of a user, each of the first stent and the second stent defining an opening extending along a centerline from an anterior end of the stent to a posterior end of the stent, wherein the centerline includes a posterior portion adjacent the posterior end, an anterior portion adjacent the anterior end, and a middle portion disposed between the posterior portion and the anterior portion, wherein the anterior portion of the centerline and the posterior portion of the centerline form an oblique angle,
   wherein the first stent and the second stent each include a nostril dome supporting protrusion extending from an outer surface of the stent adjacent the intersection of the anterior portion of the centerline and the middle portion of the centerline, wherein the nostril dome supporting protrusion extends in a direction having anterior and medial components, wherein the nostril dome supporting protrusion extends from the outer surface by a length, and
   wherein the anterior portion includes a nasal aperture portion configured to abut the nasal aperture margin when the first stent and the second stent are inserted into the nostrils of the user, wherein the nasal aperture portion has a longest width as measured perpendicular to the centerline;
wherein one of the length of the nostril dome supporting protrusion or the longest width of the nasal aperture portion is larger for the second anatomical nasal conformer device than the one of the first anatomical nasal conformer device.

11. The system of claim 10, wherein the oblique angle is in the range of 90 to 65 degrees.

12. The system of claim 10, wherein the oblique angle is in the range of 80 to 75 degrees.

13. The system of claim 10, wherein the oblique angle is a first angle, wherein the middle portion of the centerline and the posterior portion of the centerline form a second angle, wherein the second angle is in the range of 35 to 55 degrees.

14. The system of claim 10, wherein the nostril dome supporting protrusion of each of the first stent and the second stent further extend medially.

15. The system of claim 10, wherein the nostril dome supporting protrusion is configured to extend beyond the nasal aperture margin and to apply pressure to the deep margin of the lower lateral cartilage when the first stent and the second stent are inserted into the nostrils of a user.

16. The system of claim 10, wherein the first stent and the second stent each include a lateral ala vestibule protrusion extending laterally from an outer surface of the stent adjacent the anterior portion of the centerline, wherein the first stent and the second stent each include an infradome recessed portion disposed between the nostril dome supporting protrusion and the lateral ala vestibule protrusion.

17. The system of claim 10, wherein the first stent and the second stent each include a lateral ala vestibule protrusion extending laterally from an outer surface of the stent adjacent the anterior portion of the centerline.

18. The system of claim 17, wherein the lateral ala vestibule protrusion is configured to be disposed posteriorly to the nasal aperture margin and to apply pressure to a lateral aspect of the nasal vestibule when the first stent and the second stent are inserted into the nostrils of a user.

19. The system of claim 10, further comprising a central bridge extending between and coupling together the anterior end of the first stent and the anterior end of the second stent, wherein a handle protrusion extends from the central bridge.

* * * * *